(12) United States Patent
Carmi et al.

(10) Patent No.: US 9,262,845 B2
(45) Date of Patent: Feb. 16, 2016

(54) IMAGE DATA RECONSTRUCTED FROM UNDERSAMPLED HIGHER RESOLUTION AND INCOMPLETE LOWER RESOLUTION PROJECTION DATA

(75) Inventors: Raz Carmi, Haifa (IL); Amir Livne, Zichron Yaakov (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 551 days.

(21) Appl. No.: 13/703,729

(22) PCT Filed: Apr. 27, 2011

(86) PCT No.: PCT/IB2011/051850
§ 371 (c)(1),
(2), (4) Date: Dec. 12, 2012

(87) PCT Pub. No.: WO2011/161558
PCT Pub. Date: Dec. 29, 2011

(65) Prior Publication Data
US 2013/0083886 A1    Apr. 4, 2013

Related U.S. Application Data

(60) Provisional application No. 61/356,820, filed on Jun. 21, 2010.

(51) Int. Cl.
*G06T 11/00* (2006.01)
*G01N 23/04* (2006.01)
*A61B 6/00* (2006.01)

(52) U.S. Cl.
CPC ............ *G06T 11/005* (2013.01); *G01N 23/046* (2013.01); *G06T 11/006* (2013.01); *A61B 6/583* (2013.01); *G06T 2211/436* (2013.01)

(58) Field of Classification Search
CPC ............... G06T 11/006; G06T 11/005; G06T 2211/416; G06T 2211/436; G06T 2211/408
USPC ....................................................... 382/131
See application file for complete search history.

(56) References Cited

U.S. PATENT DOCUMENTS 6,437,338 B1    8/2002  Hoffman
7,054,406 B2    5/2006  Ikeda et al.
(Continued)

OTHER PUBLICATIONS

Aybat, N. S., et al.; Fast Reconstruction of CT Images from Parsimonious Angular Measurements via Compressed Sensing; 2009; http://www.columbia.edu/nsa2106/aybatPaper3_CompressedCT.pdf.
(Continued)

*Primary Examiner* — Brooke Purinton

(57) ABSTRACT

A method includes generating higher resolution image data based on undersampled higher resolution projection data and incomplete lower resolution projection data. The undersampled higher resolution projection data and the incomplete lower resolution projection data are acquired during different acquisition intervals of the same scan. A system includes a radiation source configured to alternately modulate emission radiation flux between higher and lower fluxes during different integration periods of a scan, a detector array configured to alternately switch detector pixel multiplexing between higher and lower resolutions in coordination with modulation of the fluxes, and a reconstructor configured to reconstruct higher resolution image data based on projection data corresponding to undersampled higher resolution projection data and incomplete lower resolution projection data.

20 Claims, 4 Drawing Sheets

(56) References Cited

U.S. PATENT DOCUMENTS

| | | |
|---|---|---|
| 7,103,143 B2 | 9/2006 | Alving et al. |
| 7,881,510 B2 * | 2/2011 | Doyle .......................... 382/128 |
| 8,705,828 B2 * | 4/2014 | Yang et al. ................... 382/131 |
| 8,952,333 B2 * | 2/2015 | Yu et al. .................. 250/363.03 |
| 2007/0010731 A1 | 1/2007 | Mistretta |
| 2007/0248213 A1 | 10/2007 | Dolgonos |
| 2008/0232542 A1 | 9/2008 | Lin |
| 2009/0154649 A1 | 6/2009 | Behling |
| 2009/0161932 A1 | 6/2009 | Chen |
| 2009/0161933 A1 | 6/2009 | Chen |
| 2009/0175523 A1 | 7/2009 | Chen et al. |
| 2009/0196393 A1 | 8/2009 | Wang et al. |
| 2009/0262996 A1 | 10/2009 | Samsonov et al. |
| 2009/0274355 A1 | 11/2009 | Chen et al. |

OTHER PUBLICATIONS

Chen, G-H., et al.; Prior image constrained compressed sensing (PICCS): A method to accurately reconstruct dynamic CT images from highly undersampled projection data sets; 2008; Med. Phys.; 35(2)660-663.

Gies, M., et al.; Dose reduction in CT by anatomically adapted tube current modulation: Simulation studies; 1999; Med. Phys.; 26(11)2235-2247.

* cited by examiner

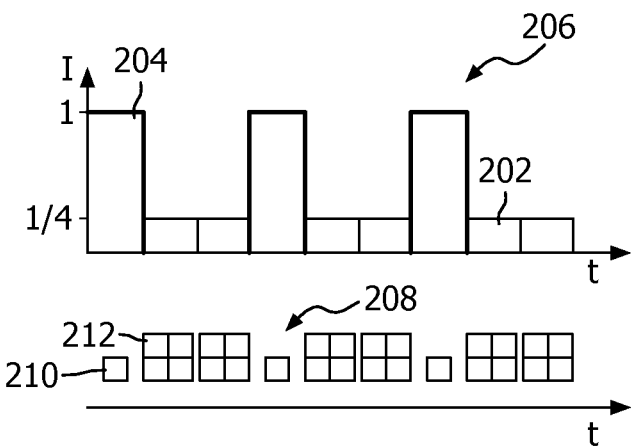
FIG. 2a
FIG. 2b
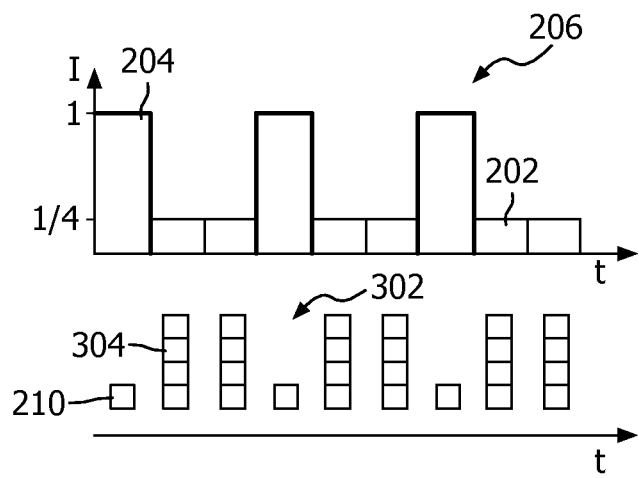
FIG. 3a
FIG. 3b
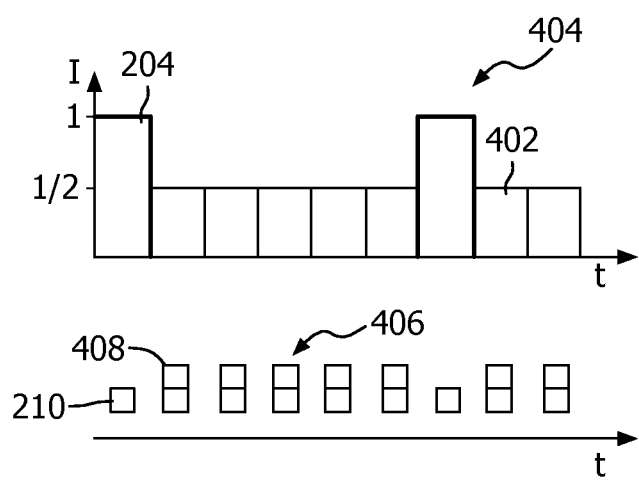
FIG. 4a
FIG. 4b

IMAGE DATA RECONSTRUCTED FROM UNDERSAMPLED HIGHER RESOLUTION AND INCOMPLETE LOWER RESOLUTION PROJECTION DATA

CROSS REFERENCE TO RELATED APPLICATIONS

This application is a national filing of PCT application Serial No. PCT/IB2011/051850, filed Apr. 27, 2011, published as WO 2011/161558 A1 on Dec. 29, 2011, which claims the benefit of U.S. provisional application Ser. No. 61/356,820 filed Jun. 21, 2010, which is incorporated herein by reference.

The following generally relates to CT data acquisition and reconstruction, and more particularly to low dose CT with high resolution reconstruction.

CT scanners emit ionizing radiation, which can cause damage to living tissue, resulting in increasing risk of cancer, tumors and genetic damage at typical doses and might cause skin burns and hair loss at high doses. As such, various approaches have been proposed to reduce patient exposure to ionizing radiation (i.e., reduce patient dose) during a CT scan.

One approach proposed in the literature has been to use compressed sensing principles. The goal is to reconstruct an artifact free tomographic image from significantly undersampled data by compensating for missing projections with additional information such as a prior image and introducing general sparsity constraints. However, in most clinical cases, CT images do not have notable sparse characteristics since the useful information is widely spread both in the image domain and in the sinogram domain.

As a consequence, in order to utilize compressed sensing methodology, a prior image, which has similar features to the target image, is required. In such cases, the difference between the two images can have sparse characteristics which can be utilized further during the dedicated reconstruction. The prior image has been, for example, a CT scan taken a short time before (or after) the target scan, like in CT perfusion; or it can be a full angular sampling low-temporal resolution image in cardiac CT. Techniques such as PICCS and HYPR are based on such prior scans.

Unfortunately, radiation dose reduction inevitably affects image noise, which is mainly dominated by the intrinsic Poissonic (or "quantum") noise of the x-ray photons arriving to the detectors. In addition, the attempt to work with very low dose in common CT systems creates significant excess image noise and artifacts. This is occurring where the electronic signals generated by the detector elements are close to the level of the electronic noise.

In current clinical practice, CT scanners are used for many different applications which may vary significantly in their requirements. For example, cardiac scans usually require high x-ray flux density for relatively short time period (achieved by high tube current) whereas lung scans can be done with very low tube current. For this reason, it is important that the radiation detectors give reliable data in both very low and high x-ray flux densities.

Conventional integrating detectors, which are based on current integration photodiodes coupled to scintillator pixels, have limited capability to detect low signals and at the same time to have wide dynamic range. Usually in that case, the noise level which is affected by both the photodiode dark current and the electronic noise is equivalent to about 10-50 mean x-ray quanta. The exact number is depended on the particular design and on the working conditions. The noise level defines the lowest detection limit since reliable detection can be done where the measured value is noticeably larger than the noise, about twice larger or more.

Conventional integrating detectors provide the full dynamic range with good linearity is usually very large and can exceed 1:100,000, but the practical problem is mainly the reliable detection of small number of x-ray quanta per single reading, i.e. in the order of magnitude of 1-100 x-ray quanta. This range of detection is crucial for working in very low x-ray doses since many views that traverse through high attenuated object can reach these low values. The low-signal problem may be even more frequent if detector arrays with especially small pixels are considered for achieving high-resolution scanners. A similar limitation can arise in double-layer detectors made for dual-energy applications, in which the radiation flux is divided between the double of the detection channels.

Aspects of the present application address the above-referenced matters and others.

According to one aspect, a method includes generating higher resolution image data based on undersampled higher resolution projection data and incomplete lower resolution projection data. The undersampled higher resolution projection data and the incomplete lower resolution projection data are acquired during different acquisition intervals of the same scan.

According to another aspect, a system includes a radiation source configured to alternately modulate emission radiation flux between higher and lower fluxes during different integration periods of a scan, a detector array configured to alternately switch detector pixel multiplexing between higher and lower resolutions in coordination with modulation of the fluxes, and a reconstructor configured to reconstruct higher resolution image data based on projection data corresponding to undersampled higher resolution projection data and incomplete lower resolution projection data.

According to another aspect, a computer readable storage medium encoded with instructions which, when executed by a processor of a computer, cause the processor to: employ a compressed sensing reconstruction algorithm to reconstruct full higher resolution image data based on undersampled higher resolution projection data and incomplete lower resolution projection data obtained from the same scan.

The invention may take form in various components and arrangements of components, and in various steps and arrangements of steps. The drawings are only for purposes of illustrating the preferred embodiments and are not to be construed as limiting the invention.

FIGS. 2-6 illustrate example radiation flux modulation/detector pixel multiplexing levels/groupings and patterns.

Figure 1:
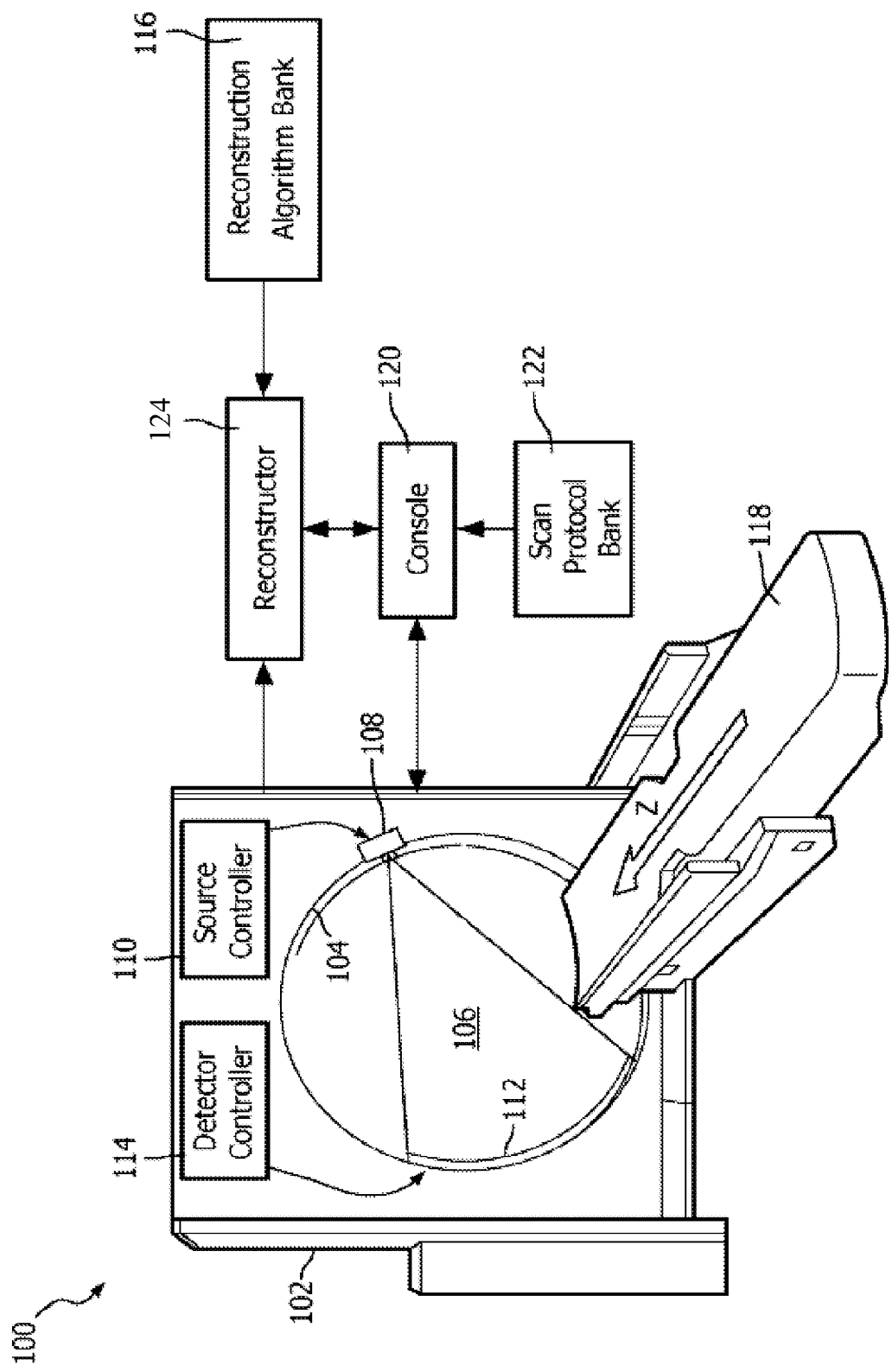
FIG. 1 illustrates an example imaging system.

FIG. 1 illustrates an imaging system 100 such as a computed tomography (CT) scanner The imaging system 100 includes a stationary gantry 102 and a rotating gantry 104, which is rotatably supported by the stationary gantry 102. The rotating gantry 104 rotates around an examination region 106 about a longitudinal or z-axis. A support 118, such as a couch, supports a subject in the examination region 106. The support 118 can be used to variously position the subject with respect to x, y, and/or z axes before, during and/or after scanning.

A radiation source 108, such as an x-ray tube, is supported by the rotating gantry 104 and rotates with the rotating gantry 104, and emits radiation. A source controller 110 controls the radiation source 108. As described in greater detail below, in one embodiment the source controller 110 can control the radiation source 108 to modulate the flux of the emitted radiation between at least first and second different fluxes during different integration intervals/periods of a scan. Where the first (or second) flux is greater than the second (or first) flux, modulating between the first and second fluxes during the scan reduces patient dose relative to the same scan in which the source 108 only emits radiation having the higher flux.

A radiation sensitive detector array 112, having a single or multiple rows of detector pixels, is located opposite the source 108 detects radiation that traverses the examination region 106 and generates projection data indicative thereof. A detector controller 114 controls the radiation sensitive detector array 112. As described in greater detail below, in one embodiment the controller 110 selectively alters the detector pixel multiplexing so that individual pixels or larger groups of the pixels are used to detect projections. Generally, individual pixels provide relatively higher resolution compared to the larger groups of the pixels.

A reconstructor 124 reconstructs projection data and generates volumetric image data indicative of the examination region 106. The reconstructor 124 can employ various reconstruction algorithms, for example, algorithms in the reconstruction algorithm bank 116 and/or other algorithms. As described in greater detail below, the reconstructor 124 can employ an algorithm in which undersampled higher resolution projection data and lower resolution reconstructed image data are used to reconstruct full higher resolution volumetric image data. Such an algorithm allows for reducing patient dose and generating full higher resolution image data, while mitigating detection limitations associated with low radiation flux.

A general purpose computing system serves as an operator console 120, which includes human readable output devices such as a display and/or printer and input devices such as a keyboard and/or mouse. Software resident on the console 120 allows the operator to control the operation of the system 100, for example, allowing the user to select a scanning technique in which the radiation emission flux is modulated and the detector pixel multiplexing is varied in coordination therewith (resulting in higher and lower resolution projection data registered in space and time) and to select a reconstruction algorithm for reconstructing full higher resolution image data from the resulting projection data.

As briefly discussed above, the source controller 110 can control the radiation source 108 to modulate the radiation flux, and the detector controller 114 can control the detector array 112 to vary pixel multiplexing. It is to be appreciated that various approaches can be utilized to do this, and that the approaches may be based on various factors such as the particular clinical application, optimization, compromises in image quality (e.g., in terms of resolution, noise, artifacts, etc.), patient radiation dose, system capabilities and performances, and/or other factors.

By way of example, pixel multiplexing can be achieved through analog multiplexing of few detector pixels into a larger effective pixel (usually groups of two or four pixels are used). In this case, the larger pixel group will have approximately the same absolute electronic noise level as the small basic pixel, but at the same time the average x-ray flux impinging onto the larger pixel group will be greater by a factor equal to the area ratio. Therefore, the signal to noise ratio is improved relative to the increase in the effective pixel area. The spatial resolution is reduced using the larger pixels.

Radiation flux modulation can be achieved by varying the temperature of an electron emitter such as a hot cathode; by powering the x-ray tube with a pulsed high voltage source to affect the electric field in between an electron source and the anode of the x-ray tube; by varying the electric field directly in front of the electron emitter; by applying electric and/or magnetic deflection of an electron beam impinging onto a surface of an anode of an x-ray tube; by using special geometrical structures of the rotating anode or by constructing the anode from different materials, etc. An approach for achieving a desired average radiation flux in a time interval is to use a very rapid repeated switching of the radiation between 'on' and 'off' states.

FIGS. 2, 3, 4, and 5 respectively illustrate non-limiting examples of modulating radiation flux and multiplexing detector pixels in coordination with each other. With FIGS. 2(a), 3(a), 4(a), and 5(a), the y-axis represents relative intensity or flux, and, with all the figures, the x-axis represents time.

In FIG. 2(a), the flux alternates between two levels 202 and 204, with the lower level 202 being one quarter of the higher level 204. The modulation pattern 206 modulates the flux so that the flux is at the higher level 204 for one integration period (acquisition interval, view, etc.) and at the lower level 202 for the next two integration periods. This pattern is repeated over time. FIG. 2(b) shows a corresponding detector multiplexing pattern 208 in which single small detector pixels 210 detect radiation during the higher levels 204, and groupings 212 of single small detector pixels detect radiation during the lower levels 202. In this example, the grouping size is four detector pixels and the grouping shape is a two dimensional array (or matrix) spanning two detector pixels along the x-axis (i.e. the angular direction of the scanner) and two rows of detector pixels along the z-axis.

With FIGS. 3(a) and 3(b), the flux modulation levels 202 and 204 and the modulation pattern 206 are the same as in FIG. 2(a). However, the multiplexing pattern 302 includes using single detector pixels 210 to detect radiation for the higher level 204 and groupings 304 of four detector pixels along the z-axis direction for the lower level 202. With FIGS. 4(a) and 4(b), a lower flux level 402 is one half of the higher flux level 204, the modulation pattern 404 modulates the flux at the higher level 204 for one integration period and at the lower level 402 for the next five integration periods, and the multiplexing pattern 406 includes using single detector pixels 210 for the higher flux level 204 and a grouping 408 of two pixels along the z-axis direction for the lower flux level 402.

Figure 5A:
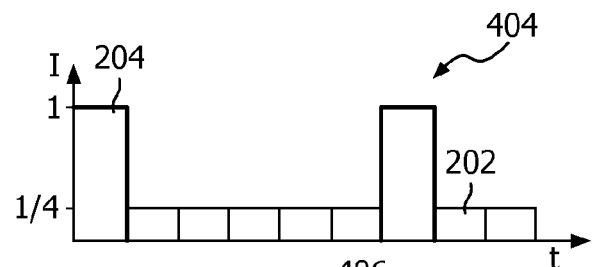
Figure 5B:
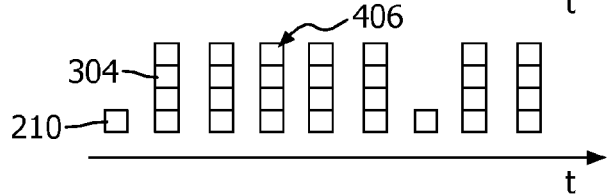

With FIGS. 5(a) and 5(b), the flux levels are the same as in FIGS. 1(a) and 2(a), the flux modulation pattern is the same as in FIG. 3(a), the pixel groupings are the same as in FIG. 2(b), and the pixel multiplexing pattern 406 is the same as in FIG. 4(b). In FIGS. 2-5, the total radiation dose respectively is reduced to 50.0%, 50.0%, 58.33%, and 37.5%, relative to the 100% dose of a scan in which the higher flux and single pixels are used for each integration period.

Note that in the above examples, the detection signal-to-noise ratio is equal to that of a standard scan in which single pixels are used in all views/integration periods and the relative radiation level is one for all views/integration periods. In other embodiments, the multiplexing may performed such that the signal-to-noise ratio is different for at least two integration periods. Furthermore, different and/or larger groupings of pixel (e.g., 6, 8, 10, 16, etc.) may be utilized. Moreover, more than two different radiation intensity levels and/or more than two different pixel groupings can be employed.

Figure 6:
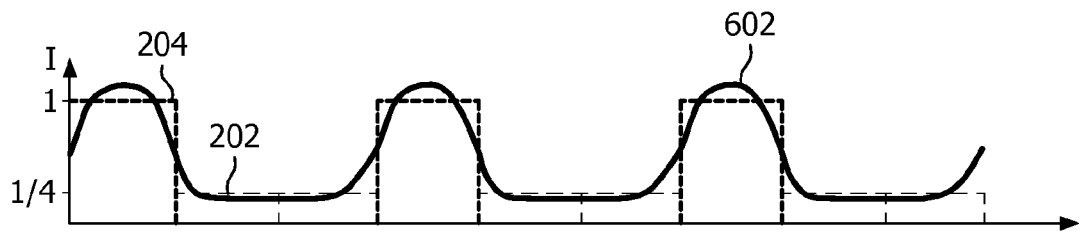

Furthermore, the time difference between two high resolution projections may be varied within the scanning duration. In addition, the x-ray spectrum may or not be changed during the scan. Moreover, the modulation phase of the radiation (or the shift of the whole sequence relative to a reference time point) can be adjustable in time. Also note that in the subject figures the x-ray intensity modulation per integration period is a step function and that somewhat slower responses (curve 602 of FIG. 6), for example, in the orders of magnitude of 10-50 micro-seconds, are also contemplated herein.

In a double-layer detector made for dual-energy applications, the multiplexing durations can be used to combine the upper and lower pixels to an effective conventional single-layer detector pixel with lower noise. The reconstruction of the different spectral images will utilize the undersampled dual energy projections and the incomplete full spectrum projections.

In one instance, the pixel multiplexing can be based on conventional CMOS switches made from complementary N-channel and P-channel CMOS transistors. By applying the required +Vc (control voltage) to the N-channel gate, and −Vc to the P-channel gate, a switch can be activated as a short or open contact. Using the configuration of N and P transistors enables to reduce the superfluous charge injection that is induced during the switching sequence. If the two transistors in the couple are well matched, a charge injection, during the switching sequence, of well below 1 fCb can be achieved. In some detector configurations the injected charge during the switching may be negligible.

In other configurations, the injected charge is not negligible and thus a special circuit should be implemented to reset this charge immediately after the switching and before a new reading is started. This can be done for example by standard techniques that are already in use today in CT detector electronics. The switching duration can be as low as several nano-seconds. However, the overall switching time, including any additional reset mechanism, can be set in accordance with the integration period. For example, where the system 100 is configured with an integration period on the order of 100-300 micro-seconds, the switching duration can be set to as much as a few micro-seconds. It should be noted that the terms 'integration period' and others are used to describe any general acquisition technique corresponding to determine the individual time durations of the plurality of imaging views.

As noted above, flux modulation and pixel multiplexing are synchronized. In one instance, this synchronization can be controlled by adjusting (e.g., during a system calibration scheme) the temporal phase of the control signal of either the radiation modulation or the pixel multiplexing. The calibration can be performed once, prior to clinical scans, or otherwise. By way of example, during the calibration procedure, the planned alternating scanning configuration is performed (in the air or on phantom) and the data are recorded. Then, the relative alternation phase is slightly changed and the measurement is repeated. An iterative sequence can be performed in order to find the phase setting in which the small pixel data achieve the highest signals among all trials, and the data of the multiplexed pixel-group achieve the lowest signals.

As noted above, the reconstructor 124 can reconstruct full higher resolution image data based on the undersampled higher resolution projection data and lower resolution reconstructed image data, which is generated from the undersampled higher resolution projection data and the incomplete lower resolution projection data. In one embodiment, the reconstruction algorithm generates the higher resolution image data by simultaneously solving EQUATIONS 1 and 2:

$$\min\|\psi(BX-X_R)\|, \quad \text{EQUATION: 1}$$

and $$\min\|MX-Y\| \quad \text{EQUATION: 2}$$

where EQUATION 1 relates to the sparsity considerations of compressed sensing, EQUATION 2 relates to the tomographic image reconstruction, $\Psi$ is a sparsifying transform, X represents the higher resolution image data, B is a blurring transform which reduces the 3D spatial resolution of X to that of $X_R$, $X_R$ are the reference well-reconstructed low-resolution image data, M is the system transform which includes all relevant scanner properties, Y are the undersampled higher resolution projection data.

In one instance, EQUATION 1 can be treated via norm minimization using a total-variation technique, and EQUATION 2 can be treated by an iterative reconstruction technique (e.g., ART, MLEM) in a sense of least squares solution or an optimization based on a Poissonic noise model. However, other suitable mathematical techniques may alternatively be used and are contemplated herein. The transform B can be a spatial image filter operated in the image voxel space, or in the Fourier transform space, where the properties of the filter are derived from the known modulation transfer functions (MTFs) of the high-resolution and the low-resolution modes. A suitable blurring transform can be a smoothing low-pass filter. The blurring transform B is embedded into the iterative solution of equation 1. A suitable scheme for such a process is shown in EQUATION 3:

$$I^{t+1}=I^t+\alpha\nabla(TV(BI^t-I_R^t)), \quad \text{EQUATION 3}$$

and

Where t stands for an iteration sequence, I represents the updated high resolution image, $I_R$ represents the reference image, B represents the blurring transform, $\alpha$ represents a pre-set parameter, TV represents the total variation operator, and the 'del' operator ($\nabla$) gives (for each voxel) the relative gradient of the total variation per a change in that voxel.

The blurring transformation B can be calculated once as a system calibration or a pre-set. Since all the required parameters are known, it can be calculated analytically or can be simulated by a computer model of the scanner. It is also possible to design a measurement calibration procedure on phantoms which can be scanned in the high-resolution and the low-resolution modes. The image characteristics can be used to find the appropriate transformation which will modify the high-resolution image to the low-resolution image.

Figure 7:
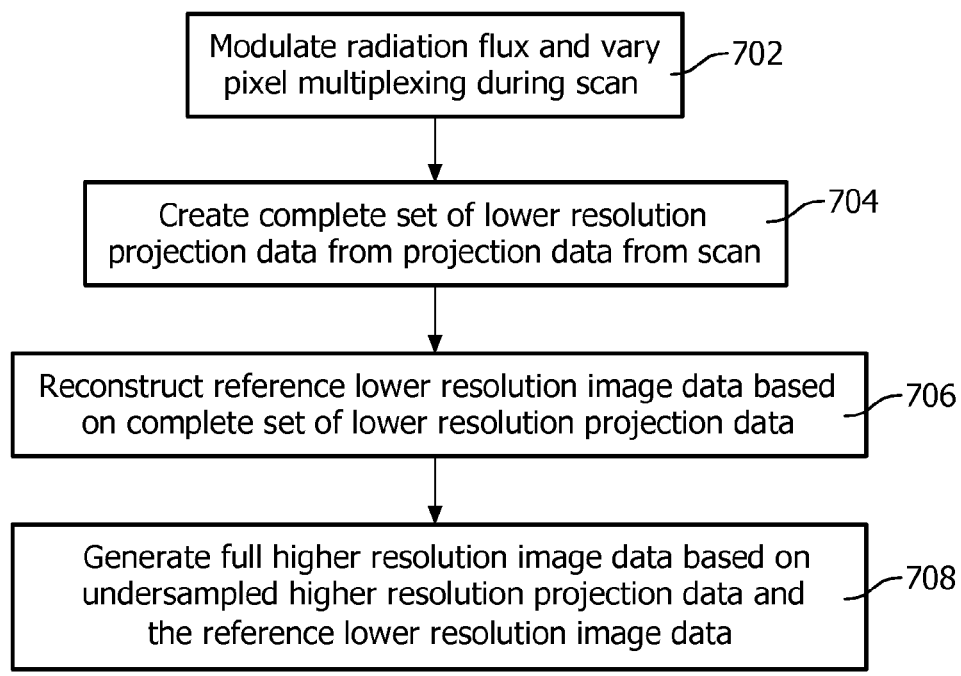
FIG. 7 illustrates an example method for reconstructing full higher resolution image data from undersampled higher resolution projection data and incomplete lower resolution projection data.

FIG. 7 illustrates a method for reconstructing higher resolution image data from undersampled higher resolution projection data and incomplete lower resolution projection data.

At 702, a scan is performed in which the radiation flux is modulated and the detector pixel are multiplexed in coordination. By way of non-limiting example, the flux modulation and detector pixel multiplexing can be as described in connection with FIGS. 2-5, a combination thereof, and/or otherwise.

At 704, the undersampled higher resolution projection data and the lower resolution projection data projection data are combined to generate a complete set of lower resolution projection data. In one instance, several spatially adjacent high resolution projection data can be combined to generate an effective low resolution projection datum.

At 706, the complete set of lower resolution projection data is reconstructed to generate reference lower resolution image data.

At 708, the undersampled higher resolution projection data and the reference lower resolution image data are utilized to reconstruct full higher resolution image data. As discussed herein, a compressed sensing reconstruction can be employed to reconstruct the full higher resolution image data, as discussed in FIG. 8 or otherwise.

Figure 8:
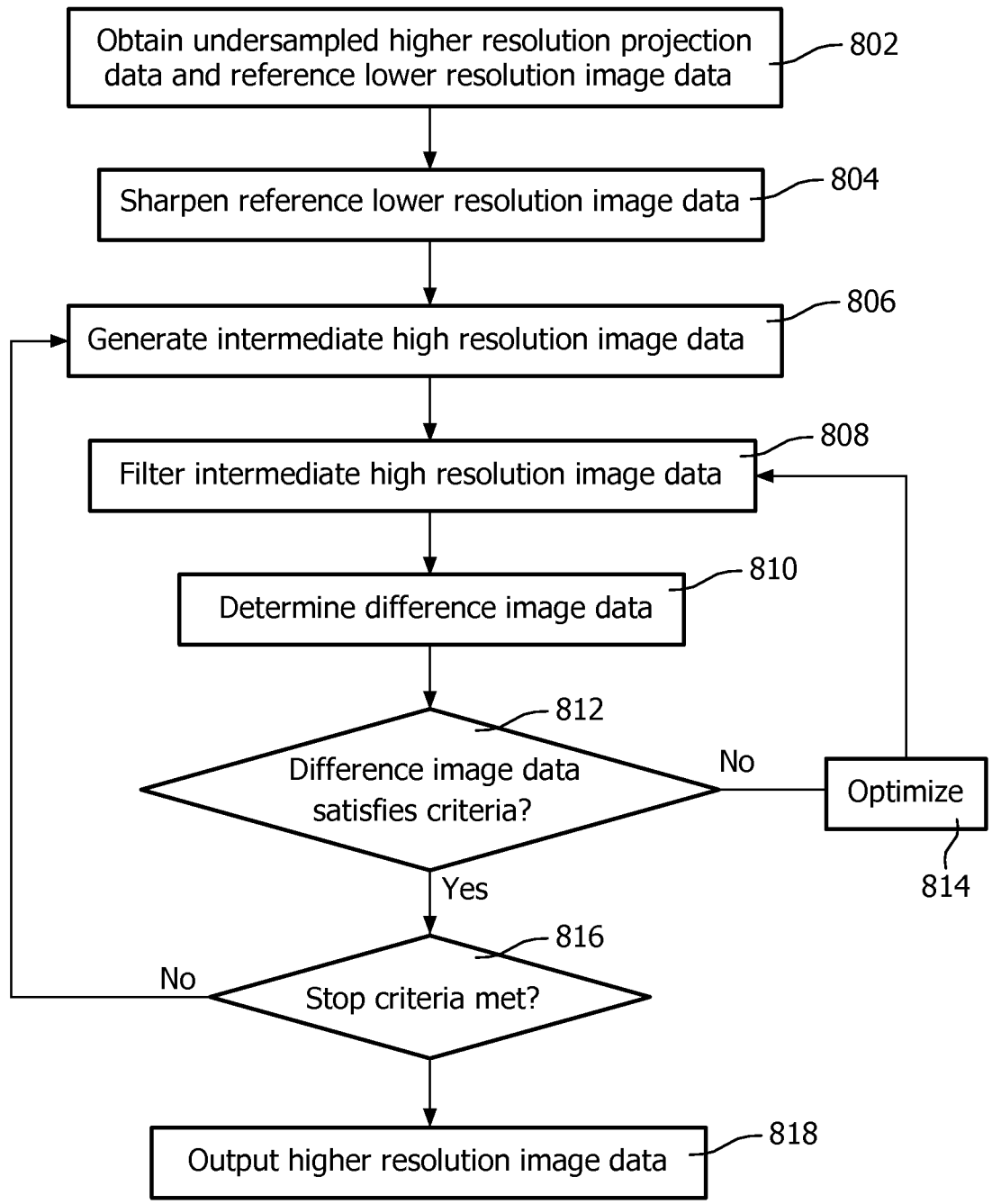
FIG. 8 illustrates an example method for reconstructing the full higher resolution image data in FIG. 7.

FIG. 8 illustrates a suitable compressed sensing flow diagram that can be used in act 708 of the method of FIG. 7.

At 802, the undersampled higher resolution projection data and the reference reconstructed lower resolution image data are obtained.

At 804, the reference reconstructed lower resolution image data is sharpened. For example, in one embodiment the reference reconstructed lower resolution image data is sharpened via a deconvolution technique that provides an initial guess to the image reconstruction.

At 806, the undersampled higher resolution projection data and the sharpen reference reconstructed lower resolution image data are utilized to reconstruct intermediate higher resolution image data. The reconstruction technique can be an iterative tomographic reconstruction.

At 808, the reconstructed intermediate higher resolution image data is filtered. For example, in one embodiment the reconstructed lower resolution image data is blurred, for example, using the blurring transformation B described herein in connection with EQUATIONS 1-3.

At 810, difference image data is generated by taking the difference between the filtered reconstructed intermediate higher resolution image data and the reconstructed lower resolution image data.

At 812, it is determined whether the difference image data satisfies predetermined criteria.

If the difference image data does not satisfy the predetermined criteria, then at 814 the intermediate higher resolution image data is optimized and acts 808 to 812 are repeated in order to generate a new intermediate higher resolution image which after the filtration at 808 becomes more similar to the reconstructed lower resolution image. The optimization may take into account reconstruction parameter, sparsity, total variation, regularization, and/or other factors. The predetermined criteria can also be a pre-determined number of iterations.

If the difference image data satisfies the predetermined criteria, then at 816 it is determined whether stop criteria is met. The criteria may include one or more of a predetermined number of iterations, a predetermined error threshold, a difference between iteration results, and/or other criteria.

If the stop criteria is not met, then acts 806-816 are repeated using the intermediate higher resolution image data which replaces the sharpen reference reconstructed lower resolution image data used for the first act of 806. Generally, the iterative process is continued where in each step the higher resolution image data becomes closer to the predetermined solution.

If the stop criteria are met, then at 818, the higher resolution image data is output.

The above described acts may be implemented by way of computer readable instructions, which, when executed by a computer processor(s), causes the processor(s) to carry out the acts described herein. In such a case, the instructions are stored in a computer readable storage medium such as memory associated with and/or otherwise accessible to the relevant computer.

Note that the terms "high," "higher," "low," and "lower" are used herein to describe relative levels, and that "higher resolution" stands for the target resolution in a particular application, and "lower resolution" stands for lower than the target resolution results in the application.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

What is claimed is:

1. A method for processing medical image data, comprising:
   generating higher resolution image data based on undersampled higher resolution projection data and incomplete lower resolution projection data, wherein the undersampled higher resolution projection data and the incomplete lower resolution projection data are acquired during different acquisition intervals of the same scan.

2. The method of claim 1, further comprising:
   completing the incomplete lower resolution projection data with the undersampled higher resolution projection data.

3. The method of claim 2, further comprising:
   reconstructing lower resolution image data based on the complete lower resolution projection data; and
   reconstructing the higher resolution image data based on the reference lower resolution image data and the undersampled higher resolution projection data.

4. The method of claim 3, further comprising:
   sharpening the reference lower resolution image data; and
   reconstructing the full higher resolution image data based on the sharpened reference lower resolution image data and the undersampled higher resolution projection data.

5. The method of claim 4, wherein the sharpening includes de-convolving the reference lower resolution image data.

6. The method of claim 3, further comprising:
   reconstructing intermediate higher resolution image data based on the reference lower resolution image data and the undersampled higher resolution projection data; and
   filtering the intermediate higher resolution image data in the process of generating the higher resolution image data.

7. The method of claim 6, wherein filtering the intermediate higher resolution image data includes blurring the intermediate higher resolution image data.

8. The method of claim 6, wherein the intermediate higher resolution image data is filtered based on MTFs corresponding to the determined high resolution scanning mode and the low resolution scanning mode.

9. The method of claim 6, further comprising:
   determining difference image data based on the filtered intermediate higher resolution image data and the reference lower resolution image data; and
   optimizing the intermediate higher resolution image data until the difference image data satisfies predetermined criteria, wherein the optimized intermediate higher resolution image data is output as the full higher resolution image data.

10. The method of claim 1, wherein the undersampled higher resolution projection data and the incomplete lower resolution projection data are acquired during an imaging procedure in which higher resolution data acquisitions and incomplete lower resolution data acquisitions are interleaved.

11. The method of claim 10, wherein the higher resolution data acquisition includes emitting radiation having first flux and detecting the radiation via a detector pixel having a first area, and the lower resolution data acquisition includes emitting radiation having second flux and detecting the radiation via two or more detector pixels combined to have a second area, wherein the first flux is greater than the second flux, and the first area is smaller than the second area.

12. The method of claim 1, further comprising:
employing a compressed sensing reconstruction algorithm to generate the higher resolution image data.

13. A medical imaging system, comprising:
a radiation source configured to alternately modulate emission radiation flux between higher and lower fluxes during different integration periods of a scan;
a detector array configured to alternately switch detector pixel multiplexing between higher and lower resolutions in coordination with modulation of the flux; and
a reconstructor configured to reconstruct higher resolution image data based on projection data corresponding to undersampled higher resolution projection data and incomplete lower resolution projection data.

14. The system of claim 13, wherein the reconstructor employs a compressed sensing reconstruction algorithm to reconstruct the higher resolution image data.

15. The system of claim 14, wherein the reconstructor reconstructs lower resolution image data based on the lower resolution projection data and the undersampled higher resolution projection data, sharpens the lower resolution image data, and generates an intermediate higher resolution image data based in part on the sharpened lower resolution image data.

16. The system of claim 15, wherein the reconstructor reconstructs intermediate higher resolution image data based on the undersampled higher resolution data and the sharpened lower resolution image data, blurs the intermediate higher resolution image data, and generates the higher resolution image data based in part on the blurred intermediate higher resolution image data.

17. The system of claim 13, wherein the detector array (112) includes a plurality of rows of detector pixels, and a smaller grouping of the pixels are employed to generate the higher resolution projection data and a larger grouping of the pixels are employed to generate the lower resolution projection data.

18. The system of claim 13, wherein a complete set of lower resolution projection data is created based on the undersampled higher resolution data and the incomplete lower resolution projection data, and the higher resolution image data is generated based in part on the complete lower resolution projection data.

19. The system of claim 13, wherein a predetermined signal to noise ratio is maintained for both the higher resolution and the lower resolution acquisitions.

20. A non-transitory computer readable storage medium encoded with computer executable instructions for processing medical image data, which, when executed by a processor of a computer, cause the processor to:
employ a compressed sensing reconstruction algorithm to reconstruct full higher resolution image data based on undersampled higher resolution projection data and incomplete lower resolution projection data obtained from the same scan.

* * * * *